United States Patent
Castillejos

(10) Patent No.: US 8,267,995 B2
(45) Date of Patent: Sep. 18, 2012

(54) METHOD AND INTRA SCLERA IMPLANT FOR TREATMENT OF GLAUCOMA AND PRESBYOPIA

(76) Inventor: David Castillejos, San Diego, CA (US)

( * ) Notice: Subject to any disclaimer, the term of this patent is extended or adjusted under 35 U.S.C. 154(b) by 0 days.

(21) Appl. No.: 10/211,197

(22) Filed: Aug. 2, 2002

(65) Prior Publication Data

US 2004/0024453 A1   Feb. 5, 2004

Related U.S. Application Data

(60) Provisional application No. 60/310,027, filed on Aug. 3, 2001.

(51) Int. Cl.
A61F 2/14 (2006.01)
(52) U.S. Cl. .............................. 623/4.1; 604/8
(58) Field of Classification Search ............ 623/4.1; 604/8
See application file for complete search history.

(56) References Cited

U.S. PATENT DOCUMENTS

| | | | |
|---|---|---|---|
| 4,457,757 A | 7/1984 | Molteno | |
| 4,634,418 A * | 1/1987 | Binder | 604/8 |
| 4,750,901 A | 6/1988 | Molteno | |
| 4,863,457 A * | 9/1989 | Lee | 604/891.1 |
| 4,936,825 A | 6/1990 | Ungerleider | |
| 4,946,436 A * | 8/1990 | Smith | 604/8 |
| 4,968,296 A | 11/1990 | Ritch et al. | |
| 5,041,081 A | 8/1991 | Odrich | |
| 5,127,901 A | 7/1992 | Odrich | |
| 5,178,604 A | 1/1993 | Baerveldt et al. | |
| 5,558,630 A * | 9/1996 | Fisher | 604/8 |
| 5,766,242 A * | 6/1998 | Wong et al. | 128/898 |
| 5,879,319 A * | 3/1999 | Pynson et al. | 604/8 |
| 6,007,578 A * | 12/1999 | Schachar | 623/11.11 |
| 6,079,417 A | 6/2000 | Fugo | |
| 6,102,045 A | 8/2000 | Nordquist et al. | |
| 6,138,307 A | 10/2000 | McDonald | |
| 6,280,468 B1 | 8/2001 | Schachar | |
| 6,299,640 B1 | 10/2001 | Schachar | |
| 6,383,218 B1 | 5/2002 | Sourdille et al. | |
| 6,383,219 B1 | 5/2002 | Telandro et al. | |
| 2002/0123804 A1 * | 9/2002 | Gwon et al. | 623/4.1 |
| 2002/0138139 A1 * | 9/2002 | Till | 623/4.1 |
| 2003/0033015 A1 * | 2/2003 | Zhou et al. | 623/6.64 |
| 2006/0116759 A1 * | 6/2006 | Thornton et al. | 623/4.1 |

FOREIGN PATENT DOCUMENTS

| | | |
|---|---|---|
| WO | WO 9640005 A1 * | 12/1996 |
| WO | WO 0056255 A1 * | 9/2000 |
| WO | WO 00/74600 A1 * | 12/2000 |

OTHER PUBLICATIONS

Fukasaku, H. et al. "Anterior Ciliary Sclerotomy with Silicone Expansion Plug Implantation: Effect on Presbyopia and Intraocular Pressure": International Ophthalmology Clinics, Spring 2001, 41(2), 133-141.*

* cited by examiner

Primary Examiner — David H Willse
Assistant Examiner — Javier Blanco
(74) Attorney, Agent, or Firm — Donn K. Harms

(57) ABSTRACT

An intra scleral implant and method of implantation for use in the treatment of intraocular pressure and presbyopia. The implant features a body portion and protrusions from the body portion to anchor the device in a cavity formed in the scleral wall of the eye. Optionally a drug delivery function is provided to allow long term communication of drugs to tissue surrounding the implant.

4 Claims, 2 Drawing Sheets

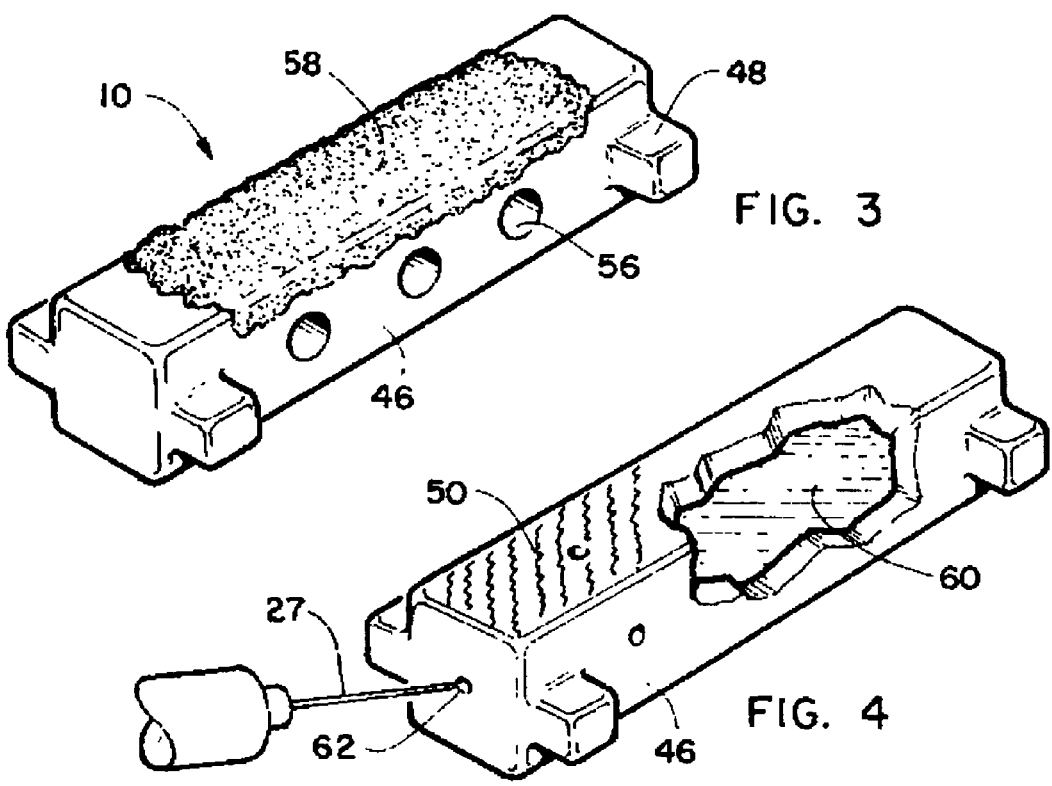
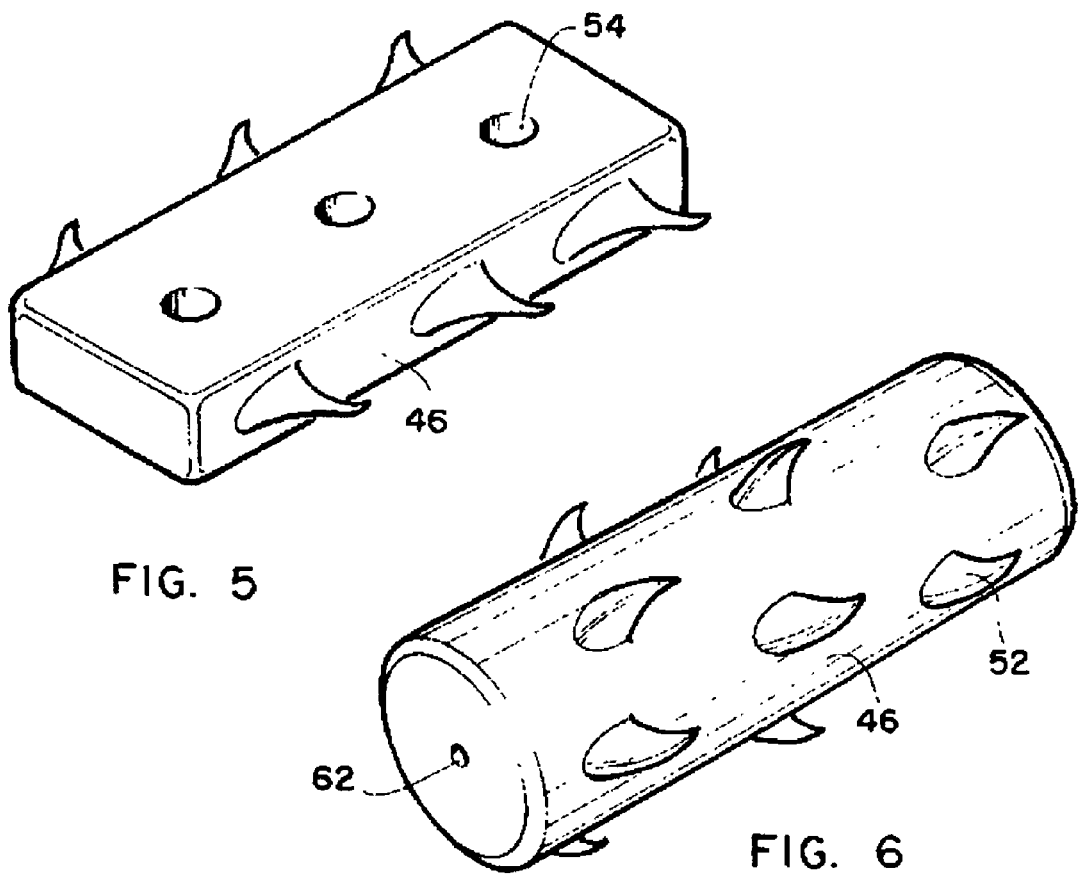

METHOD AND INTRA SCLERA IMPLANT FOR TREATMENT OF GLAUCOMA AND PRESBYOPIA

This application claims the benefit of U.S. Provisional Application No. 60/310,027 filed Aug. 3, 2001.

BACKGROUND OF INVENTION

1. Field of Invention

The disclosed device relates to a scleral implant. More particularly it relates to a device which is implanted in the sclera of the eye for the treatment of excess intraocular pressure which frequently accompanies Glaucoma and for the treatment of presbyopia or loss of accommodation of the eye.

Glaucoma is an eye disease wherein the patient gradually loses sight. Such vision loss is caused by damage to the optic nerve which acts like an electric cable and communicates images from the eye to the brain. High intraocular pressure frequently accompanies Glaucoma and is one of the main causes of the nerve damage causing this vision loss. It is thought that increased intraocular pressure is caused when the eye's drainage canals become clogged over time. The intraocular pressure rises to levels causing damage because the correct amount of fluid can't drain out of the eye in the normal fashion. If this excess intraocular pressure is not detected and treated, it can cause a gradual loss of vision. Such a vision loss in some cases occurs over a long period of time. However, in some cases of glaucoma the eye pressure usually rises very fast. It is thought that this happens when the eye drainage canals are blocked or covered over, like the clog in a sink when something is covering the drain.

Drugs are frequently used on cases where intraocular pressure slowly builds and frequently work well. In patients suffering a rapid rise in such pressure or a long term rise that has reached a dangerous plateau, severe eye damage and permanent loss of sight can result.

Surgery has also been used more recently to treat intraocular pressure. Clinical investigators have noted in recent years that intraocular pressure is lowered following radial incisions in the anterior sclera, known as an anterior ciliary sclerotomy. Unfortunately, for patients undergoing such a procedure, the beneficial effects are negated over a period of time following the procedure as the incisions heal and scar. Consequently the potential for eyesight loss arises as pressure again builds following the surgery.

Another sight related problem affecting patients is that of Presbyopia which is a vision condition in which the crystalline lens of a patient's eye loses its flexibility. flexibility makes it difficult for a person to focus on close objects. While Presbyopia may seem to occur suddenly once the patient discovers the problem, it is generally accepted that the cause of the sight loss is actual loss of flexibility of the lens which takes place over a number of years and usually becomes noticeable in the early to mid-forties.

Treatment to help you compensate for presbyopia includes prescription reading glasses, bifocals, contact lenses, and laser surgery. However such corrective lenses can be inconvenient to the wearer and laser surgery to the cornea of the eye carries with it the inherent risk to the eyesight itself if a mistake is made.

Still further, many diseases that attack the eye and eyesight require the long term administration of drugs to maintain eyesight. It is desirable to provide an easily placed device that would provide long term modulated direct communication of drugs into the eye concurrently with helping correct the internal pressure and possible vision problems of the patient.

Consequently, there is a continuing need for a medical treatment that would a require simple surgical procedure that would have long-lasting effects to relieve internal eye pressure and for the correction of presbyopia to eliminate or reduce the need for prescription lenses and without risky surgery on the lens of the eye itself. Such a treatment would be further enhanced by the provision of a drug delivery system that can be modulated for dose and time that would aid in internal pressure relief as well as other eye ailments requiring precision or long term delivery of drugs.

2. Prior Art

Surgical procedures and implantable devices have recently been developed to address the presbyopia.

U.S. Pat. No. 6,280,468 (Schachar) discloses a scleral prosthesis for treatment of presbyopia and other eye disorders. Schachar teaches the placement of a prostheses in a plurality of pockets slightly smaller than the implant, circumferentially around the pupil, to exert an outward pressure on the sclera thereby restoring the working distance of the ciliary muscle allowing the patient relief from presbyopia. However, Schachar is oriented circumferentially around the pupil or front of the eye and lacks an anchoring means to hold the implants in proper position in the sclera over the long term which can result in shifting of the implant reducing or eliminating its effectiveness. Further, the use of tunnels smaller than the implant tends to cause broken implants. Schachar also lacks a drug delivery means from the implant. Still further, actual dismounting of the implant can occur which would require removal from the eye especially if it pierces the outside surface of the eye when shifting in position. Additionally, the circumferential placement of the implants is not as effective at encouraging internal drainage and reduction of intraocular pressure.

U.S. Pat. No. 6,102,045 (Nordquist) discloses a method and apparatus for lowering intraocular pressure of the eye. However Nordquist is a filtering implant which extends into the anterior chamber of the eye through an opening in the limbus cornea. Nordquist lacks the ability to correct presbyopia that a sclera-mounted device provides and because of its delicate positioning and communication directly with the anterior chamber Nordquist is harder to position correctly. It also lacks the ability to infuse drugs to the eye and the provision of direct communication between the anterior chamber and the exterior regions of the eye increases the risk of infection to the anterior chamber.

U.S. Pat. No. 6,079,417 (Fugo) discloses a method and device for reshaping the cornea to change its topography. However Fugo lacks the ability to increase the drainage from the eye interior to lower intraocular pressure. Fugo also is designed to mount directly into the cornea layer of the eye.

U.S. Pat. No. 5,178,604 (Baerveldt) teach the use of an implant for increasing eye drainage and reduce pressure caused by glaucoma. However Baerveldt is simply a tube which communicates directly with the interior chamber of the eye and offers no aid to rectifying presbyopia.

As such, there is a continuing need for a reliable operative method and prostheses that will aid physicians in interrupting the relentless cycle that results in vision loss and eye damage to patients suffering from building intraocular pressure in the eye. Such a device should be insertable into the eye in a relatively easy procedure for a trained surgeon. Such a device and procedure should avoid the more delicate structures of the eye and should also avoid communicating internal eye structures directly with the exterior of the eye to prevent infection. Such a device would provide additional utility by through the optional ability to provide a drug delivery system from the implant directly to the eye. Still further, the device implanted by this method should be dimensioned with an anchor structure to insure that the implant stays properly positioned in perpetuity thereby alleviating the need for replacement or removal caused by dislocatable implants and maintaining a fixed correction of vision.

SUMMARY OF THE INVENTION

The above problems, and others are overcome by the herein disclosed method and intra-sclera implant for the treatment of glaucoma and presbyopia. The method of insertion of the implants requires incisions be made radially in the anterior sclera. A plurality of such incisions are made radially and only into the sclera with the current best number of incisions being four, with one incision in each quadrant of the eye.

Once the incisions are made in the proper quadrants and extend properly toward the rear of the eye, one implant is positioned within the space of each of the incisions. The scleral incision is then closed by opposition or using suture or other means of closure of the incision to urge the scleral flap toward the surface of the eye from where it was detached and reattach it to the sclera.

The implant is currently best formed in a unitary construction and formed of a material that is inert when in contact with body tissue. Favored materials include one or a combination of materials from a group including hydroxiapartite, silicone, polymethylmethacrylate, acrylic, and tantalum.

The unitary body of the implant can optionally be serrated or have one or a plurality of apertures running through to contact scleral tissue and anchor it. Additionally, the body of the implant can also be impregnated with a drug which thereafter would be slowly delivered into the tissue of the eye or have an internal reservoir or coating of a slowly disburseable drug that can be modulated for dose and time frame to allow for long term delivery of medication to the eye and body of the patient, from the implant.

Accordingly, it is the object of this invention disclosed herein to provide a reliable method of surgery for the placement of implants in the sclera is easy to accomplish for the trained surgeon.

It is another object of this invention to provide an implant that is easily insertable into the scleral layer of the eye during a surgical procedure.

It is still another object of this invention to provide such an implant that has an anchoring system to insure that the implant maintains the position intended by the surgeon implanting it.

Yet another object of this invention is the provision of a method and apparatus for eye surgery that may be used to treat presbyopia as well as rising intraocular pressure.

Still further, it is an object of this invention to provide such an implant with the option of long term drug delivery directly from the implant to the eye.

These and further objectives of this invention will be brought out in the following part of the specification, wherein detailed description is for the purpose of fully disclosing the invention without placing limitations thereon.

BRIEF DESCRIPTION OF THE DRAWING FIGURES

The accompanying drawings which are incorporated in and form a part of this specification illustrate embodiments of the disclosed device and together with the description, serve to explain the principles of the invention.

FIG. 3 depicts a preferred embodiment of the implant showing anchors and optional coating.

FIG. 4 depicts another preferred embodiment of the device having an internal reservoir for holding a drug to be communicated to the exterior.

FIG. 5 depicts another preferred embodiment of the device showing anchors about the exterior.

FIG. 6 depicts another preferred embodiment of the device showing a round body and anchors extending from the surface.

DETAILED DESCRIPTION OF THE PREFERRED EMBODIMENTS OF THE DISCLOSED DEVICE

Figure 1:
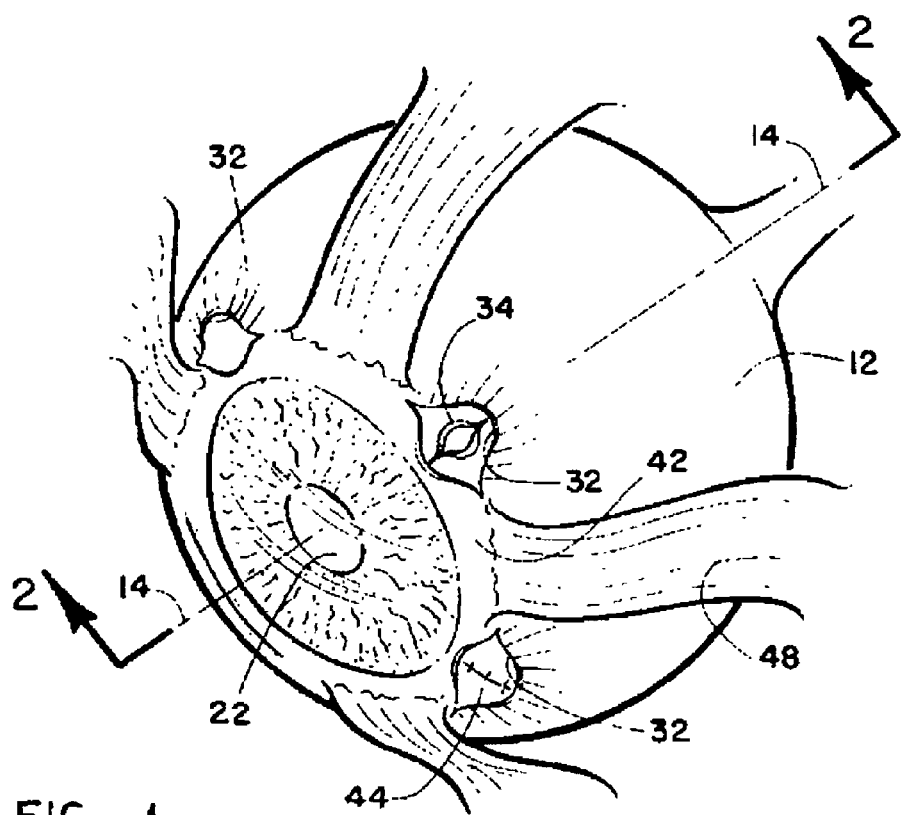
FIG. 1 depicts the placement of a plurality of implants radially in four quadrants of the eye and the steps of the method to do so.
Figure 2:
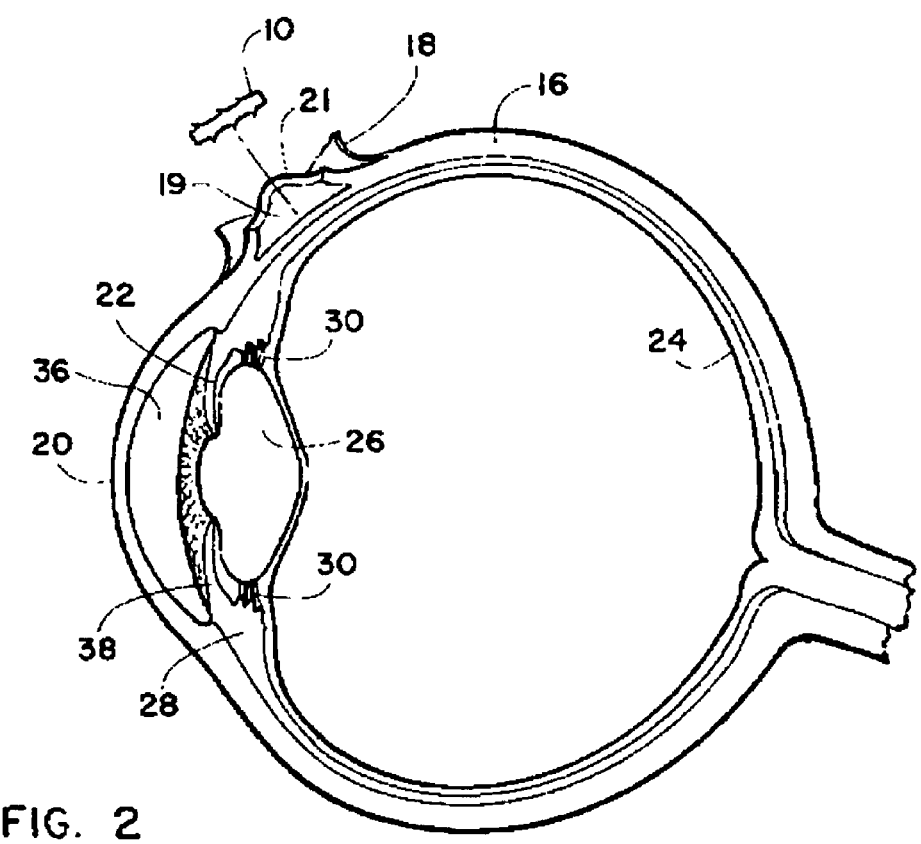
FIG. 2 shows the implant and its placement in the scleral layer of the eye.

Referring now to FIGS. 1-6 depicting the preferred embodiments of the disclosed device 10, FIG. 1 depicts the preferred location and steps in the operative method for the placement of the device 10 into the eye 12. The method for surgical insertion of the implant device 10 requires incisions be made radially in the sclera 16 in relation to the cornea 22 and generally in line with the center axis 14 of the eye 12 depicted as running along line 2-2 in FIG. 1.

In its basic structure the eye 12 consists of a globe having an outer coat, a middle layer and an inner layer. The outer coat is made up of a tough fibrous, white layer—the sclera 16, which communicates with the conjunctiva 18 which is a mucous membrane that lines the inner surfaces of the eyelids and folds back to cover the front surface of the eyeball, except for the central clear portion of the outer eye which is the cornea 20. The middle layer contains pigment and forms the iris 22. The inner layer is the light seeing layer or retina 24. The lens 26 is an oval disc which sits behind the iris 22. It is conventional belief that the cornea 20 focuses approximately two-thirds of the light entering the eye 12 and the lens 26 about one third. Lens accommodation or focusing is by simple explanation accomplished by the ciliary muscle 28 pulling upon zonules 30 communicating between the ciliary muscle 28 and the lens 26.

As people age, many suffer from Presbyopia which is a vision condition in which the lens 26 loses some of its flexibility, or the zonules 30 become elongated making it harder for the ciliary muscle 28 to focus the lens 26 as needed. Through implanting the device 10 using the surgical method herein disclosed, it is thought that the rejoined sclera 16 tends to pull over the device 10 and impart resulting tension to the ciliary muscle 28 giving it more working distance or travel and resulting ability to pull upon the lens 26 for better accommodation as patients receiving the device using the method of implantation have had improved vision thereafter. It is also thought that a decrease in the lens 26 equatorial diameter and a slight stretching of the zonules 30 increasing their working range also results from the scleral tension developed by the rejoining of the sclera 16 over the inserted device 10, all combine to increase amplitude of accommodation following the implantation surgery.

Intraocular pressure in the eye 12 is caused by a build up of fluid in the anterior chamber 36 and posterior chamber 38 when that fluid which is naturally produced in the eye 12, fails to be communicated through the trabecular meshwork (similar to the grate on a manhole) into the Canal of Schlemm which is the sewer system duct of the eye getting rid of excess fluid and the waste products of the eye. It has been found that following the procedure using the aforementioned method of implantation of the device 10 in the eye of patients, that the drainage of aqueous fluid from the eye increases resulting in a drop of intraocular pressure. As best can be understood, the apparent tightening of the sclera 16 after implantation of the device in the four quadrants of the eye 12, apparently has a tightening or tensioning effect on the ciliary muscle 28 and its connection to the lens 26 and concurrently helps to improve the flow of fluid through the trabecular meshwork in the same region to aid in evacuation of fluid from the anterior chamber 36 and posterior chamber 38. Of course other explanations may be apparent to those skilled in the art and such are anticipated however in the current best mode patients do experience a drop in fluid pressure in the eye subsequent to the implantation of the device 10 using the method herein disclosed.

In exercising the surgical method for insertion of the implant device 10 the surgeon would begin with a small limited conjunctival peritomy as shown by the conjunctival incisions 32 of FIG. 1. In the current best mode of the method a plurality of conjunctival incisions 32 are performed with four being the current best number, with one in each quadrant of the eye 12 located in-between the muscles 48 attached to the exterior of the eye 12. The conjunctival incisions 32 expose the sclera 16 wherein next, in each conjunctival incision 32, a radial incision 34 is made radially or generally inline with the axis 14 of the eye 12 running through the center of the iris 22 and out the back of the eye 12. The radial incisions 34 it has been found, are best made posteriorly 0.5 mm from the limbus and measuring substantially 3 mm in length and approximately 600 microns in depth. However it does depend upon the dimensions of the device 10 implanted and the size of the radial incisions may change to accommodate differently dimensioned devices 10. Such an substantial inline orientation of the radial incisions 34 to the axis 14 or radial to the circle forming the iris 22, has been found to produce the best results for both accommodation and increased drainage of the eye 12.

Once the radial incisions 34 are complete and correctly axially oriented and positioned in the aforementioned manner, an implant device 10 is positioned within the space formed by the radial incision 34. At this point the radial incision 34 may be closed using a means of closure such as a suture 44 which pulls the scleral flap 21 over the implant device 10 when so rejoined exerting tension upon the sclera 16 and to communicating structures of the sclera 16. Those skilled in the art will recognize that other means of closure of such incisions are available and new means are continually being discovered and the use of such is anticipated. A radial cavity 19 is formed when the scleral flap 21 is rejoined to the sclera which surrounds the implant device 10 was placed in the radial incision. It is also anticipated that the implantation of the implant device 10 radially oriented away from the cornea 20 might be done in other fashions such as drilling or injection or in the future, with a laser or means of mechanization, and such is anticipated. The important aspect of the device and method herein described is that the implant device 10 is placed radially oriented and surrounded by the sclera in a formed cavity and the current best mode of achieving a radial cavity 19 to hold the implant device 10 radially oriented respective to the cornea 20 is by the surgical method herein described.

Following closure of the radial incisions 34, the conjunctival incisions 32 are closed using cautery or other means of such closure. The method now being complete, the implant device 10 is properly placed to improve both the vision and fluid drainage of the patient. The implant device 10 may be removed in the reverse order.

The implant device 10 used in combination with the surgical method, in the current best mode, is formed of a material that is inert when in contact with body tissue. The implant device 10 as noted, occupies the radial cavity 19 formed when the radial incision 34 is closed in the aforementioned method. A tightening or tensioning of the sclera 16 layer is provided when the radial incision 34 is closed and the scleral flap 21 is sutured or otherwise rejoined with the sclera 16 and stretched over the implant device 10 during closure. Favored materials include one or a combination of materials from a group including hydroxiapartite, silicone, polymethylmethacrylate, acrylic, and tantalum. Those skilled in the art will recognize that other materials could be used and new materials are continually being developed for implants and the use of such is anticipated.

The implant device 10 has body portion 46 and a means to anchor the device in radial cavity 19 to substantially prevent movement, which in a current preferred embodiment is provided by anchors 48 protruding from the body portion 46. Other means to anchor the device when placed in the radial cavity could accomplished be through the use of a serrated surface 50, or curved projections 52, or detents 54 in the exterior surface of the body 46 or apertures 56 which would communicate through the body 46. Or, one or combinations of such means to prevent movement of the implant device 10 can be used together.

Optionally, should the delivery of drugs to the point of implantation be desirable, which with many illnesses such localized delivery is, the device 10 can be provided with a means to communicate drugs from a device resident supply of drugs, to the device to the surrounding eye tissue. This drug delivery system can be provided by one or a combination of micro encapsulated drug coatings or other polymer or prolonged dissolving coatings 58 on the exterior of the device, or through a reservoir 60 inside the body 46 which would hold a supply of the drug of choice in either solid or liquid form and communicate the drugs through channels 62 to the surrounding tissue. Or the material from which the device 10 is produced can be impregnated with the appropriate drug and secrete the same over time. When a reservoir 60 is used, the dosage and delivery time can be modulated by adjusting the amount of communication achieved through the channels 62 or just as the coating can, by adjusting the polymer or other substance in which the drug is dissolved to yield dissolution that will deliver the dose for amount of time desired for infusion. From the reservoir 60 the device would secrete the drugs over a determined period at the determined dose and then can be refilled through a channel 62 by a hypodermic needle 27 which would pierce the sclera 16 and refill the reservoir 60 through one of the channels 62 or a similar passage designed for such a refill. Refill can thus be accomplished without the need for the implant device 10 to be removed or disturbed from its secure mount inside the radial cavity 19.

FIG. 6 depicts the device 10 with a body 46 that is round or barrel shaped rather than the cube or rectangular shape of FIGS. 3-5. The body 46 would work well in either configuration so long as one of the noted anchoring means projects from it to anchor the device 10 in the radial cavity. While the curved projections 52 are shown on all sides, it may be beneficial in some cases to omit them from one side for smooth transition of the scleral flap 21 over the implant device 10.

While all of the fundamental characteristics and features of the present invention have been described herein, with reference to particular embodiments thereof, a latitude of modification, various changes and substitutions are intended in the foregoing disclosure and it will be apparent that in some instance, some features of the invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined by the following claims.

What is claimed is:

1. A method for lowering the intraocular pressure of an eye or treating presbyopia by surgically placing an implant comprising the steps of:

making a small limited conjunctival peritomy in the eye to expose the sclera;

making a plurality of four elongated incisions, each oriented in a radial direction of the eye, in the anterior sclera to form four scleral flaps;

positioning a plurality of four elongated scleral implants, each having a body with a longitudinal axis, within the spaces formed by the radially oriented incisions such that the longitudinal axis of each of said elongated scleral implants is oriented in said radial direction of the eye, in said incisions; and reattaching the scleral flap over each of said elongated scleral implants, to the sclera, and suturing each of said incisions to thereby form a cavity within the sclera completely surrounding each of said elongated scleral implants, whereby tension is imparted to said sclera by stretching of said sclera surrounding said body to form said cavity to accommodate said body positioned therein and a stretching of said flap over said body for said reattaching, thereby aiding in relieving said intraocular pressure by enhancing natural fluid flow to the trabecular meshwork of the eye;

wherein each of said scleral implants comprises means to anchor each body in each of said elongated incisions, whereby movement of said elongated body in said elongated incision is substantially prevented.

2. The method of claim 1, wherein said implants additionally comprise:

means to communicate a drug dose to surrounding tissue from an implant-resident supply of said drug.

3. The intra-scleral implant of claim 1, wherein each of said bodies is formed of substantially inert material when implanted.

4. The intra-scleral implant of claim 1, wherein each of said bodies is formed of silicone or acrylic and has a low coefficient of thermal expansion.

* * * * *